US00PP31199P2

(12) United States Plant Patent
Bean et al.

(10) Patent No.: US PP31,199 P2
(45) Date of Patent: Dec. 10, 2019

(54) ***TECOMARIA* PLANT NAMED 'DWOY001'**

(50) Latin Name: *Tecomaria capensis*
Varietal Denomination: DWOY001

(71) Applicant: Charles Andrew de Wet, Johannesburg (ZA)

(72) Inventors: Quinton Bean, Johannesburg (ZA); Charles Andrew de Wet, Johannesburg (ZA)

(73) Assignee: Charles Andrew De Wet, Johannesburg (ZA)

( * ) Notice: Subject to any disclaimer, the term of this patent is extended or adjusted under 35 U.S.C. 154(b) by 0 days.

(21) Appl. No.: 16/350,150

(22) Filed: Oct. 3, 2018

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Tecomaria capensis* named 'DWOY001', that is characterized by its compact plant habit, its small plant size, and its flowers that are orange in color with a yellow throat.

1 Drawing Sheet

Botanical classification: *Tecomaria capensis*.
Varietal denomination: 'DWOY001'.

CROSS REFERENCE TO RELATED APPLICATIONS

This application is related to U.S. Plant Patent for a plant derived from the same breeding program that is entitled *Tecomaria* Plant Named 'DWOR001' (U.S. Plant patent application Ser. No. 16/350,148), *Tecomaria* Plant Named 'DWRE001' (U.S. Plant patent application Ser. No. 16/350,151), *Tecomaria* Plant Named 'DWPI001' (U.S. Plant patent application Ser. No. 16/350,152), and *Tecomaria* Plant Named 'DWYE001' (U.S. Plant patent application Ser. No. 16/350,149).

BACKGROUND OF THE INVENTION

The present invention relates to a new and distinct cultivar of *Tecomaria capensis* and will be referred to hereafter by its cultivar name, 'DWOY001'. 'DWOY001' represents a new cape honeysuckle, a sub-tropical shrub grown for landscape use.

The new cultivar was derived from a controlled breeding program by the Inventor in Hartebeespoort, North West Province, South Africa. The Inventor made a cross in September of 2013 between unnamed proprietary plants from the Inventor's breeding program as both the female parent and male parent. The Inventor selected 'DWOY001' as a single unique plant amongst the seedlings that resulted from the above cross in September of 2014.

Asexual propagation of the new cultivar was first accomplished by the Inventor by stem cuttings in October 2014 in Hartebeespoort, North West Province, South Africa. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'DWOY001' as a unique cultivar of *Tecomaria capensis*.

1. 'DWOY001' exhibits a compact plant habit.
2. 'DWOY001' exhibits a small plant size.
3. 'DWOY001' exhibits flowers that are orange in color with a yellow throat.

Both the female and male parent plant of 'DWOY001' differ from 'DWOY001' in having flowers that are mono tone apricot in color. 'DWOY001' can also be compared to the *Tecomaria capensis* cultivars 'Lutea' (not patented) and 'Apricot' (not patented) and cultivars from the same breeding program; 'DWRE001', 'DWOR001', 'DWPI001', and 'DWYE001'. 'Lutea' is similar to 'DWOY001' in having a compact plant habit but differs from 'DWOY001' in having flowers that are solid yellow in color. 'Apricot' is similar to 'DWOY001' in growth rate but differs from 'DWOY001' in having a larger plant size and in lacking a compact plant habit. 'DWRE001', 'DWOR001', 'DWPI001', and 'DWYE001' are similar to 'DWOY001' in having short plant heights and compact plant habits. 'DWRE001' differs from 'DWOY001' in having flowers that are red in color. 'DWOR001' differs from 'DWOY001' in having orange flowers. 'DWPI001' differs from 'DWOY001' in having salmon pink flowers. 'DWYE001' differs from 'DWOY001' in having yellow flowers.

BRIEF DESCRIPTION OF THE DRAWING

The accompanying colored photograph illustrates the overall appearance and distinct characteristics of the new *Tecomaria*, 'DWOY001'. The photograph was taken of a one-year-old plant as grown outdoors in a 2-gallon container in Loxley, Ala. The photograph provides a view of the inflorescences of 'DWOY001'.

The colors in the photograph are as close as possible with the digital photography and printing techniques utilized and the color codes in the detailed botanical description accurately describe the new *Tecomaria*.

DETAILED BOTANICAL DESCRIPTION

The following is a detailed description of the new cultivar taken from one-year-old plants as grown outdoors in 2-gallon containers in Loxley, Ala. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Sub-tropical bush; can be deciduous to evergreen depending on climate.

*Plant habit.*—Compact, upright and spreading.

*Height and spread.*—An average of 45 cm in height and 38 cm in spread as grown in a 2-gallon container and reaches 1.3 meters in height and 1.5 m in spread in the landscape.

*Cold hardiness.*—U.S.D.A. Zone 7a.

*Diseases and pests.*—No susceptibility or resistance to diseases or pests has been observed.

*Root description.*—Fine and fibrous, 162D in color.

*Growth rate.*—Moderate to vigorous.

*Propagation.*—Stem cuttings.

*Root development.*—2 to 4 weeks to initiate roots and an average of 6 weeks to fully root as a young plant from a rooted cutting.

Branch description:

*Branch shape.*—Rounded, slightly oval.

*Branching and size.*—An average of 2 lateral branches; average of 23 cm in length and 5 mm in width, an average of 2 secondary stems per lateral branch; an average of 15 cm in length and 2.7 mm in width.

*Branch surface.*—New growth; glabrous and semi-glossy with lenticels; about 15 per stem 1.5 cm in length, about 0.5 mm in length, and 155A in color, mature stems; finely vertically ridged with lenticels; an average of 30 per stem 2.5 cm in length, about 1.5 mm in length, and 161C in color.

*Branch strength.*—Strong.

*Branch arrangement.*—Secondary branches primarily opposite.

*Branch aspect.*—Lateral branches primarily upright, secondary branches held at an average angle of 45° from the lateral stems.

*Internode length.*—Average of 2 cm.

*Branch color.*—New growth 144A, maturing; a blend of 147A and 199A, mature; vertical ridges 199B and 197A.

Foliage description:

*Leaf arrangement.*—Opposite or whorls of 3.

*Leaf shape.*—Oblong overall.

*Leaf division.*—Odd-pinnate, typically 7 leaflets (occasionally 5).

*Leaf size.*—An average of 6.5 cm in length and 4.5 cm in width.

*Leaf quantity.*—About 17 per stem 18 cm in length.

*Leaf aspect.*—Leaf and leaflets are slightly curled downward.

*Leaflet base.*—Cuneate to slightly oblique.

*Leaflet apex.*—Terminal acuminate, laterals acute.

*Leaflet venation.*—Pinnate, color: upper surface matches leaf surface, lower surface 144D.

*Leaflet shape.*—Broadly elliptic to ovate.

*Leaflet margins.*—Crenate.

*Leaflet surface.*—Glabrous, upper surface satiny, lower surface dull.

*Leaflet color.*—New and mature growth upper surface 137B, new and mature growth lower surface; a blend of 138A and 138B.

*Leaflet size.*—An average of 2.9 cm in length and 1.7 cm in width.

*Petiole and rachis.*—Petiole; (from base to lowest leaflet) an average of 1.5 cm in length and 1 mm in width, rachis; (from lowest leaflet to top of rachis) an average of 2.8 cm in length and 1 mm in length, petiolules; none sessile to rachis, both are slightly sulcate on upper surface, 137C in color and moderate in strength with glabrous surfaces.

Inflorescence description:

*Inflorescence type.*—Panicles on terminals and upper nodes.

*Inflorescence size.*—Average of 7 cm in height and 8.5 cm in width with 6 blooms open with some small flower buds unopened at apex.

*Flower buds.*—Narrowly obovate in shape and curved slightly downward, an average of 4 cm in length and 1 cm in width (at apex), color a blend of 23A and 13B.

*Flower fragrance.*—None.

*Lastingness of flowers.*—About 5 days.

*Flower aspect.*—Nearly upright to outward and slightly nodding downward.

*Flower quantity.*—An average of 7 per inflorescence with 3 per peduncle node.

*Flower shape.*—Tubular with petal lobes spreading.

*Flower type.*—Single, tubular (bilabiate in appearance).

*Flower size.*—Average of 5.5 cm in length and 3.2 cm in diameter.

*Peduncles.*—Oval in shape, an average of 4 cm in length and 1.5 mm in diameter, strong, held upright, and 137B in color, surface glabrous with lenticels; not conspicuous, an average of 6 per 1 cm×3 mm, oblong in shape, average of 0.3 in length, 138D in color, no secondary peduncles or peduncle leaves present.

*Pedicels.*—Average of 1 cm in length and 1 mm in diameter, held at 15° to vertical, moderately strong and 137B in color.

*Calyx.*—Campanulate in shape, an average of 1 cm in length and 5 mm in diameter, persistent.

*Sepals.*—5, fused with free apices; acute apex with mucronate tip, 2 mm in length and width, entire margin, both surfaces smooth and dull, color of outer surface 145A with stripes and base 138C, color inner surface 145A.

*Petals.*—5, lower 70% fused into tube, tube; an average of 4.3 cm in length and 1 cm in width (at apex), glabrous and slightly satiny on outer surface, short glistening hairs with ridges due to adnate stamens on inner surface, color on outer surface a blend of 23A and 13B, color inner surface a blend of 16C and 13B with filaments of adnate stamens 2C, lobes; oblong in shape, margin entire and very slightly wavy, apex obtuse, base fused to tube, color outer and inner surface a blend of 23A and 13B, 1.6 cm in length and 1 cm in width, upper 2 petals; lower 40% fused together, held upright and slightly reflexed, lower 3 petals; held outward and strongly reflexed, corona not persistent.

Reproductive organs:

*Gynoecium.*—1 pistil, about 5.5 cm in length, style is an average of 4.5 cm in length, and 1C in color, stigma is club-shaped, 1 mm in diameter, and 145D in color, ovary is oblong in shape, 3 mm in length and 145C in color.

*Androecium.*—5 stamens, anthers are dorsifixed, 2-lobed, narrow oblong in shape, lobes 3 mm in length and 2B in color, filaments are an average of 6 cm in length and 1C in color with lower 40% adnate to petals, pollen is moderate in quantity and 160B in color.

*Fruit and seed.*—No fruit or seed production has been observed to date.

It is claimed:

1. A new and distinct cultivar of *Tecomaria* plant named 'DWOY001' as herein illustrated and described.

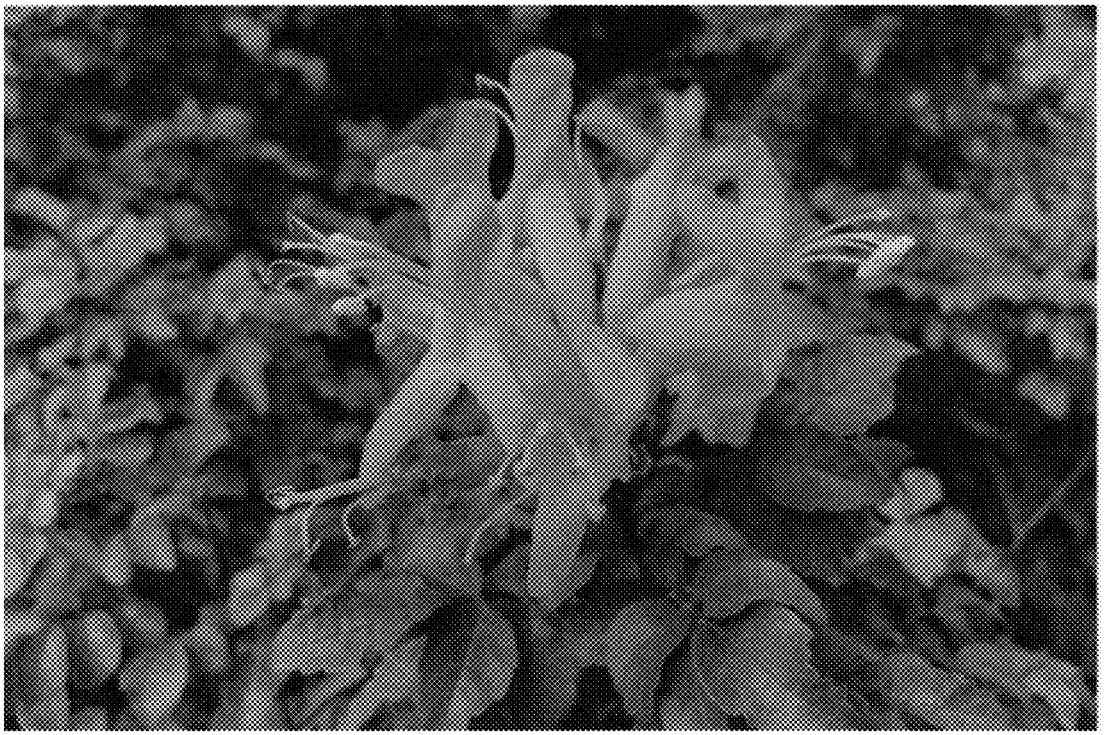

* * * * *